(12) United States Patent
Nicoletti et al.

(10) Patent No.: US 8,947,669 B2
(45) Date of Patent: Feb. 3, 2015

(54) OPTICAL GAS DETECTOR

(71) Applicant: Commissariat à l'énergie atomique et aux énergies alternatives, Paris (FR)

(72) Inventors: Sergio Nicoletti, Sinard (FR); Pierre Barritault, Grenoble (FR); Mickaël Brun, Eybens (FR)

(73) Assignee: Commissariat à l'Energie Atomique et aux Energies Alternatives, Paris (FR)

( * ) Notice: Subject to any disclaimer, the term of this patent is extended or adjusted under 35 U.S.C. 154(b) by 0 days.

(21) Appl. No.: 14/032,084

(22) Filed: Sep. 19, 2013

(65) Prior Publication Data
US 2014/0078504 A1    Mar. 20, 2014

(30) Foreign Application Priority Data
Sep. 20, 2012 (FR) ..................... 12 58832

(51) Int. Cl.
| | | |
|---|---|---|
| G01N 21/00 | (2006.01) | |
| G01N 21/61 | (2006.01) | |
| G01N 21/3504 | (2014.01) | |
| G01N 21/03 | (2006.01) | |

(52) U.S. Cl.
CPC ............ *G01N 21/61* (2013.01); *G01N 21/3504* (2013.01); *G01N 21/0303* (2013.01)
USPC ............................ 356/437; 356/433; 356/411

(58) Field of Classification Search
CPC .......................................................... G01B 9/02
USPC ................................................. 356/433–441
See application file for complete search history.

(56) References Cited

U.S. PATENT DOCUMENTS

| | | | |
|---|---|---|---|
| 5,401,966 A | 3/1995 | Gray et al. | |
| 6,797,944 B2 * | 9/2004 | Nguyen et al. | 356/36 |
| 7,119,337 B1 | 10/2006 | Johnson et al. | |
| 2011/0190605 A1 | 8/2011 | Yamashita et al. | |

OTHER PUBLICATIONS

Institut National De La Propriete Industrielle, Preliminary Search Report, dated Jun. 20, 2013 for FR12/58832.

* cited by examiner

*Primary Examiner* — Tarifur Chowdhury
*Assistant Examiner* — Iyabo S Alli
(74) *Attorney, Agent, or Firm* — Kevin R. Erdman; Brannon Sowers & Cracraft PC

(57) ABSTRACT

A gas detector including: an assembly of two coaxial parabolic reflective caps having opposite concavities, and a wafer arranged in the focal plane of the two caps, at the center of this focal plane, comprising, back-to-back: a diverging light emitter directed towards the first cap and a light receiver directed towards the second cap, wherein the two caps are distant substantially by the sum of their focal distances plus the thickness of the wafer.

7 Claims, 2 Drawing Sheets

OPTICAL GAS DETECTOR

CROSS-REFERENCE TO RELATED APPLICATION

The present application claims priority under 35 U.S.C. §119 of French Patent Provisional Application Serial Number 12/58,832, filed Sep. 20, 2012, the disclosures of which are incorporated by reference herein.

BACKGROUND

The present disclosure relates to an optical detector of the presence, and possibly of the content, of a gas in an atmosphere.

STATE OF THE ART

The use of optical detectors of the presence of a gas, for example, carbon dioxide $CO_2$, carbon monoxide CO, methane, or possibly various toxic gases such as xylene or toluene released by paints, is known. It should be noted that a detector of the presence of an excess of $CO_2$ may form a fire detector.

Optical detectors which detect the presence of a gas by measuring the absorption of a light beam at one or several wavelengths corresponding to one or several absorption lines of the considered gas will here be considered. In such detectors, an optical beam is emitted by a light source emitting in a wavelength range comprising the wavelength of absorption lines characteristic of the gas to be detected. A receiver preceded by a filter at the wavelength of the absorption line to be detected indicates the absorption at this wavelength, and the presence and the content of the considered gas can be deduced therefrom. For such detectors to operate satisfactorily, two receivers or two receive areas are generally provided, the second receiver being intended to provide a reference indication at wavelengths other than the wavelength of the absorption line. This reference is especially used to take into account environmental fluctuations and/or intensity fluctuations in the emission source.

So that the entire gas detection system can have a small bulk, it is often provided for the light beam propagating between the emitter and the receiver to travel one or several times back and forth via reflector systems. It is for example provided for laser beams to undergo multiple reflections in a resonant cavity where the gas to be detected is likely to be present.

Generally, existing gas detection systems implying at least one back and forth travel of light beams between the emitter and the receiver have the disadvantage of being relatively delicate to manufacture. Indeed, they require an accurate positioning of the emitter and of the receiver with respect to the reflective surfaces determining the optical path between the emitter and the receiver.

There thus is a need for an optical absorption gas detector which is particularly simple to manufacture and which is tolerant to misalignments between the emitter, the reflective surfaces, and the receiver.

SUMMARY

An embodiment provides a device overcoming at least some of the disadvantages of existing devices.

To achieve this, an embodiment provides a gas detector comprising an assembly of two coaxial parabolic reflective caps having opposite concavities, and a wafer arranged in the focal plane of the two caps, at the center of this focal plane, comprising, back-to-back: a diverging light emitter facing the first cap and a light receiver facing the second cap, wherein the two caps are distant substantially by the sum of their focal distances plus the thickness of the wafer.

According to an embodiment, the two parabolic caps are connected to a mount setting the distance between them.

According to an embodiment, the mount is a cylinder.

According to an embodiment, the light receiver comprises at least two portions detecting different wavelengths.

According to an embodiment, the wafer is supported by a tab maintained by a mount for assembling the caps, the tab being located in the focal plane of the caps.

According to an embodiment, the tab is made of a material transparent to the wavelengths that the gas detector aims at detecting.

According to an embodiment, the light emitter and receiver are formed in plate portions having their rear surfaces placed against each other.

According to an embodiment, the plates are made of a material transparent to the wavelength likely to be detected, and are placed against each other with an interposed layer of an opaque material.

According to an embodiment, the opaque material is a metal.

According to an embodiment, the metal is pierced with an opening providing a direct optical communication between the emitter and at least one of the receivers.

According to an embodiment, a gas detector comprises an assembly of two coaxial parabolic caps (1-1, 1-2) having opposite concavities, and a wafer (11) arranged in the focal plane of the two caps, at the center of this focal plane, comprising, back to back: at least one diverging light emitter (AB) directed towards the first cap (1-1), and at least one light receiver (CD) directed towards the second cap (1-2). The two caps are distant substantially by the sum of their focal distances plus the thickness (d) of the wafer. Further, the wafer is formed of portions of plates (20, 22) of a material transparent to the wavelength likely to be detected, and are placed against each other with an interposed layer of an opaque material pierced with an opening (36) providing a direct optical communication (38) between the emitter and one at least of the receivers. The detector may have the opaque material as a metal (30). The detector may have the two parabolic caps connected to a mount setting the distance between them. The detector may have the mount as a cylinder (39). The detector may have the light receiver (CD) comprising at least two portions detecting different wavelengths. The detector may have the wafer (11) supported by a tab (40) maintained by a mount for assembling said caps, said tab being located in said focal plane of said caps. The detector may have the tab (40) made of a material transparent to the wavelengths that the gas detector aims at detecting.

BRIEF DESCRIPTION OF THE DRAWINGS

The foregoing and other features and advantages will be discussed in detail in the following non-limiting description of specific embodiments in connection with the accompanying drawings.

Figure 1:
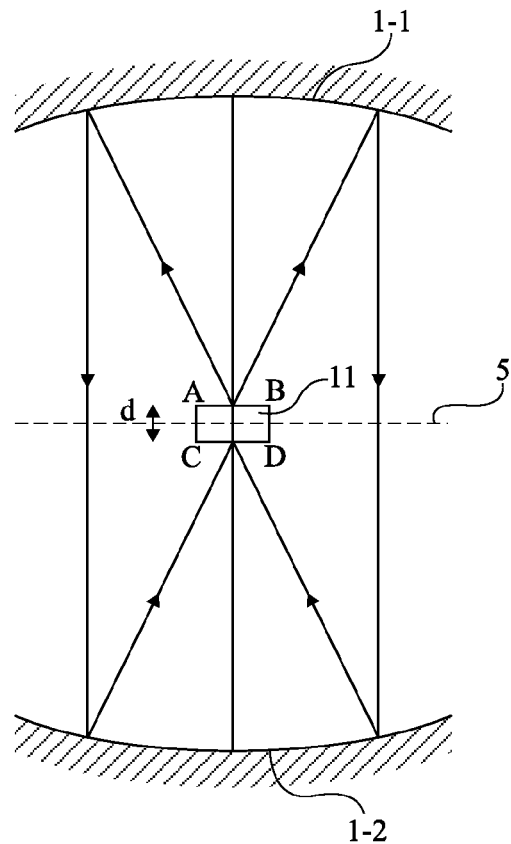
FIG. 1 is a cross-section view of an embodiment of an optical gas detector tolerant to misalignments.

Corresponding reference characters indicate corresponding parts throughout the several views. Although the drawings represent embodiments of the present invention, the drawings are not necessarily to scale and certain features may be exaggerated in order to better illustrate and explain the present invention. The exemplification set out herein illustrates an embodiment of the invention, in one form, and such exemplifications are not to be construed as limiting the scope of the invention in any manner.

DETAILED DESCRIPTION

The embodiments disclosed below are not intended to be exhaustive or limit the invention to the precise form disclosed in the following detailed description. Rather, the embodiments are chosen and described so that others skilled in the art may utilize their teachings.

FIG. 1 is a cross-section view showing an embodiment of an absorption gas detector according to an embodiment.

The detector comprises two coaxial parabolic caps 1-1 and 1-2 having opposite concavities. The parabolic caps are substantially confocal. Thus, the image of a point placed on a surface of the focal plane forms on the opposite surface of this focal plane.

An emitter-receiver assembly 11 is arranged at the level of common focal plane 5 of the two parabolic caps. Emitter-receiver assembly 11 is shown in the form of a small plate having an emitting surface AB facing one of parabolic caps 1-1 and a receiving surface CD facing opposite parabolic cap 1-2. Thus, the image of the emitter forms on the receiver. Calling d the thickness of plate 11, the axial distance between the tops of the two parabolic caps will be equal to the sum of their focal distances plus thickness d.

Simulations performed by the inventors show that such a system is practically insensitive to misadjustments to a certain extent. Such simulations have especially enabled to draw up the following table:

| Motion | Displacement Amplitude (μm) | Relative power on receiver | Spot motion in the receiver plane (μm) |
|---|---|---|---|
| The two mirrors move by the same quantity in the same direction and laterally. | 0 | 100 | 0 |
| | 10 | 100 | 20 |
| | 20 | 95 | 40 |
| | 30 | 83 | 60 |
| | 40 | 68 | 80 |
| The mirror on the source side or the mirror on the receiver moves alone laterally. | 0 | 100 | 0 |
| | 10 | 100 | 10 |
| | 20 | 100 | 20 |
| | 30 | 99 | 30 |
| | 40 | 95 | 40 |
| The two mirrors move by the same quantity in the same direction or in opposite directions and in depth. | 50 | 95 | |
| | −50 | 95 | |
| The mirror on the source side or the mirror on the receiver side moves alone in depth. | −100 | 97 | |
| | +100 | 97 | |

If the source and the receiver are displaced together, this has but little influence on the capacity of the system to operate properly if the source is in the axis of symmetry of the optical system. Similarly, if the source is brought a little closer to the first hemisphere, it can be observed that the rays are still focused on the receiver, provided for it to have followed the motion of the source. The provided device thus offers a certain geometric stability.

Further, for lateral displacements, the image spot does not deform and displaces in the image plane. If a single mirror is displaced by a distance x, the spot displaces by the same value x on the receiver. If both mirrors are displaced by a distance x each, the spot displaces by 2× on the receiver. For a displacement in depth, the image spot remains centered and only its diameter varies.

Such a large positioning tolerance is especially due to the fact that the emitting portion, on side AB, and the receiving portion, on side CD, of emitter-receiver assembly 11 are assembled head-to-tail in a single block, whereby the emitter and the receiver(s) displace together and this simultaneous displacement compensates for the consequences of possible mispositionings.

Figure 2A:
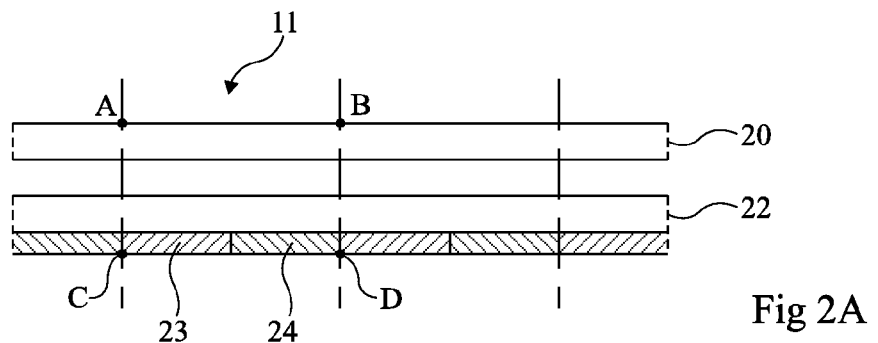
FIG. 2A is a cross-section view at an intermediate stage of the assembly of an embodiment of an emitter-receiver-filter assembly.

FIG. 2A illustrates, as an example, a step of manufacturing an example of embodiment of an emitter-receiver assembly 11. Many emitters are formed on a first plate 20, for example, a silicon plate or a plate of an insulating material such as sapphire.

The emitter preferably is a non-directional or little directional emitter (diverging emitter) such as a heated filament This emitter will not be described in detail since its manufacturing technology is well known. It may be a platinum or titanium nitride filament formed on the plate by any known means. In operation, the filament is heated up to a temperature capable of providing a sufficient quantity of radiation in a wavelength range containing the absorption line to be detected. This temperature is preferably greater than 250° C., for example, ranging between 350° C. and 650° C. for a detection wavelength of 4.25μm in the case where the gas to be detected is $CO_2$. Advantageously, such a temperature is compatible with a long lifetime of the filament.

The receivers on the CD side of device 11 are formed on a second plate 22, also by any known means. The second plate preferably is a silicon plate having passive components (resistors) or active components (diodes or transistors) having characteristics which are variable according to their heating on reception of infrared rays. In particular, the receivers may be bolometric receivers, for example formed of a membrane which absorbs infrared rays and thus heats up, the temperature rise of the membrane implying a variation of its detectable resistance, or also temperature sensors or thermocells.

Each receiver on the side of surface CD may be coated with at least one filter. Two filters 23, 24 are shown in the cross-section view of FIG. 2A, respectively centered on the absorption line to be detected and on a reference wavelength. These filters may correspond to stacks of thin dielectric layers. They may also be an alternation of metallic and insulating strips having a step and a spacing determining the filtering frequency.

Then, plates 20 and 22 are placed against each other so that surfaces AB and CD form opposite external surfaces, and are sawn into elementary wafers, each corresponding to an emitter-receiver assembly, according to the sawing lines illustrating in vertical dotted lines in FIG. 2A. The mechanical junction between plates 20 and 22 may be formed by means of an adhesive layer providing a permanent connection, for example, made of a polymer or of a gold/tin (AuSn) or aluminum/silicon (AlSi) alloy. It should be noted that the forming of a metal layer between the two substrates is used to form a shield for the receiver so that it is not disturbed by the source radiation if the substrates used are transparent in infrared.

Figure 2B:
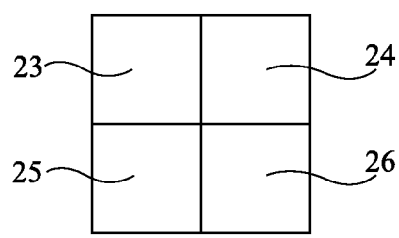
FIG. 2B is a partial top view of an element of the assembly of FIG. 2A.

The bottom view of FIG. 2B shows a case where four filters 23, 24, 25, 26 intended, for example, to respectively receive a reference wavelength or wavelength range and three specific wavelengths or wavelength ranges, for example corresponding to three absorption lines or bands of a same gas to be detected or to absorption lines or bands of several gases to be detected, have been provided. Each filter is associated with a receiver, for example, of bolometric type. Plate 11 for example has a side length ranging from 1 to 5 mm and a thickness ranging from 0.5 to 1.5 mm.

Figure 2C:
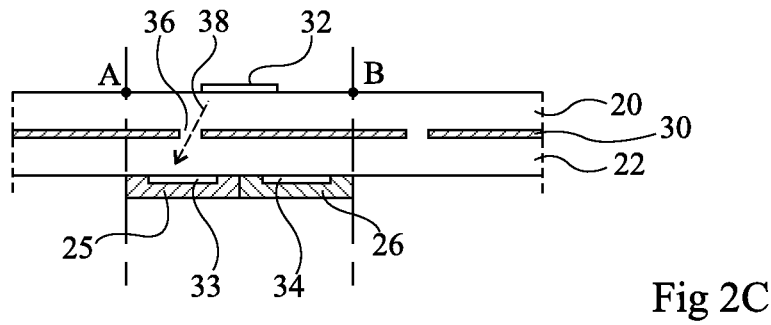
FIG. 2C is a cross-section view of an alternative embodiment of an emitter-receiver-filter assembly.

FIG. 2C is a cross-section view of an alternative embodiment of an emitter-receiver-filter assembly. In certain cases, plates 20, 22 are transparent to the concerned wavelengths. Such is for example the case for silicon wafers and wavelengths close to 4.25 µm. This is also more generally the case for most semiconductor materials such as Ge, SiGe, CdSe, AsGa, InP etc. which are transparent at least in certain infrared radiation ranges. In this case, it is provided to place a layer forming a barrier against the transmission of direct radiations through the plates, between the emitter and the receiver(s). A layer 30 opaque to radiations, for example, a metal layer, formed on at least one of the two plates before assembly thereof, may for example be provided, as shown.

In the representation of FIG. 2C, a rectangle 32 symbolizes the emitter area on surface AB of the upper plate and rectangles 33, 34 are used to symbolize two receiver areas on surface CD of the lower plate, respectively covered with filters 25, 26. Opaque layer 30 comprises, in an alternative embodiment, an opening 36 for giving way to a direct radiation 38 from emitter 32 to receiver 33. In this variation, "filter" 25 covering receiver 33 is then opaque. Receiver 33 then provides a reference signal representative of the sole fluctuations of emitter 32.

Figure 3:
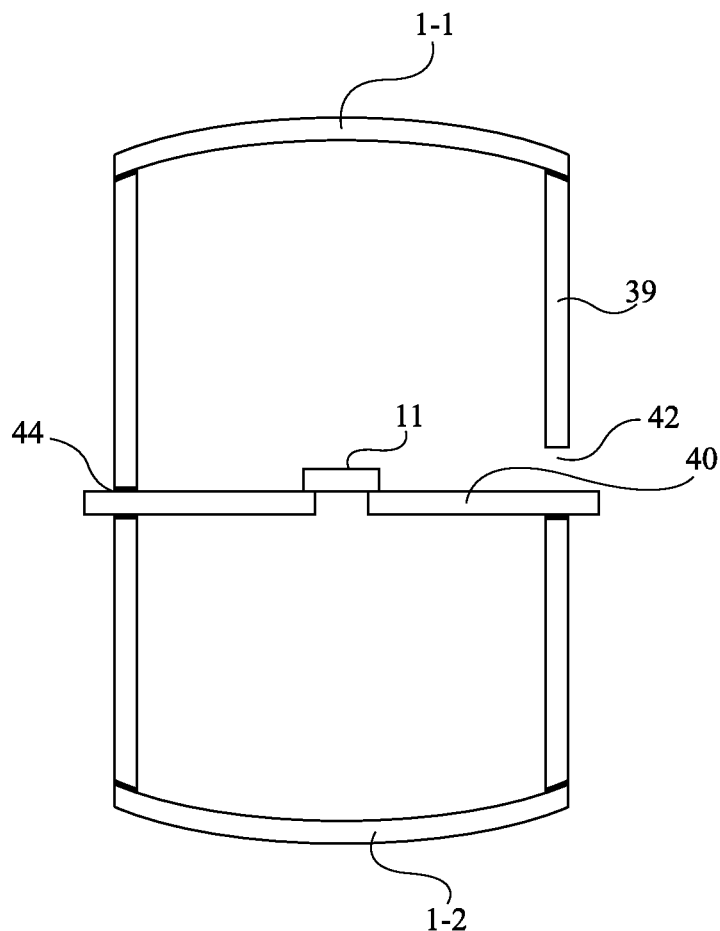
FIG. 3 is a perspective view of an embodiment of an optical absorption gas detector.

FIG. 3 is a cross-section view showing an example of assembly of emitter-receiver block 11 inside of a mount maintaining parabolic caps 1-1 and 1-2 in position. The mount is for example formed of a cylinder 39 having parabolic caps 1-1 and 1-2 attached at its ends, for example, by gluing. The cylinder has a height such that the axial distance between the centers of the parabolic caps is equal to twice the focal distance of these caps plus thickness d of emitter-receiver 11. It should be noted that other shapes may be used for the mount.

Wafer 11 is assembled on a tab 40 having metal tracks (not shown) intended to provide the connections to the emitter and to the receiver(s) running thereon. The tab may be made of a transparent material in the wavelength range to be detected, for example of silicon or sapphire, such materials being substantially transparent to a 4.25-µm wavelength. Tab 40 may also comprise, opposite to wafer 11, an opening intended to give way to light rays towards the receiver(s).

In the shown example, which is not limiting, tab 40 bears on an opening 42 of mount 39 and engages into a diametrically opposite opening 44 of the mount.

It should be understood that the present invention is likely to have many alterations, as concerns the number of optical emitters, the number of optical receivers and of associated filters, as well as the nature of these emitters and receivers and the forming of the head-to-tail assembly of an emitter and of receivers.

Further, the metal deposition enabling to make the inner surfaces of the parabolic caps reflective may be performed so that the reflective surface is slightly rough to blur the image of the filament on the receiver.

Although, in the drawings, the focal distances of parabolic caps 1-1 and 1-2 are shown as being substantially equal, it should be noted that these focal distances may be clearly different, so that the image of the emitter on the receiver(s) is reduced or enlarged. This selection will especially be made according to the manufacturing technique used.

Although this has not been described, it should be understood that the mount, for example, cylinder 39, is perforated to let the inside of the enclosure defined by the cylinder and the spherical caps communicate with the outside.

Although the mount intended to provide the relative positioning of the two parabolic caps 1-1 and 1-2 has been described and shown as a cylinder, it should be noted that any mount may be used. Pillars may for example be used, for example, three pillars connecting the two caps, these pillars having settable dimensions to enable a fine adjustment of the system.

It will be within the abilities of those skilled in the art to freely select the dimensions of the detector according to the components used, to the gases to be detected, and to their concentrations. For example, in the case of a detector block such as that shown in FIG. 3, the longitudinal dimension may range from 5 to 10 cm and the diameter may range from 1 to 3 cm.

Such alterations, modifications, and improvements are intended to be part of this disclosure, and are intended to be within the spirit and the scope of the present invention. Accordingly, the foregoing description is by way of example only and is not intended to be limiting. The present invention is limited only as defined in the following claims and the equivalents thereto.

What is claimed is:

1. A gas detector comprising:
    an assembly of two coaxial parabolic caps having opposite concavities, and
    a wafer arranged in the focal plane of the two caps, at the center of the focal plane, comprising, back to back:
    at least one diverging light emitter directed towards the first cap, and
    at least one light receiver directed towards the second cap,
    wherein the two caps are distant substantially by the sum of their focal distances plus the thickness of the wafer, and
    wherein the wafer is formed of portions of plates of a material transparent to the wavelength corresponding to the absorption line of the gas to be detected, and are placed against each other with an interposed layer of an opaque material pierced with an opening providing a direct optical communication between the emitter and one at least of the receivers.

2. The detector of claim 1, wherein the opaque material is a metal.

3. The detector of claim 1, wherein the two parabolic caps are connected to a mount setting the distance between them.

4. The detector of claim 3, wherein the mount is a cylinder.

5. The detector of claim 1, wherein the light receiver comprises at least two portions detecting different wavelengths.

6. The detector of claim 1, wherein the wafer is supported by a tab maintained by a mount for assembling said caps, said tab being located in said focal plane of said caps.

7. The detector of claim 6, wherein the tab is made of a material transparent to the wavelengths that the gas detector aims at detecting.

* * * * *